(12) United States Patent
Karasawa et al.

(10) Patent No.: US 10,551,737 B2
(45) Date of Patent: Feb. 4, 2020

(54) METHOD FOR FORMING RESIST UNDERLAYER FILM

(71) Applicant: NISSAN CHEMICAL INDUSTRIES, LTD., Tokyo (JP)

(72) Inventors: Ryo Karasawa, Toyama (JP); Tetsuya Shinjo, Toyama (JP); Keisuke Hashimoto, Toyama (JP)

(73) Assignee: NISSAN CHEMICAL INDUSTRIES, LTD., Tokyo (JP)

( * ) Notice: Subject to any disclaimer, the term of this patent is extended or adjusted under 35 U.S.C. 154(b) by 0 days.

(21) Appl. No.: 15/554,403

(22) PCT Filed: Feb. 5, 2016

(86) PCT No.: PCT/JP2016/053534
§ 371 (c)(1),
(2) Date: Aug. 29, 2017

(87) PCT Pub. No.: WO2016/143436
PCT Pub. Date: Sep. 15, 2016

(65) Prior Publication Data
US 2018/0046078 A1 Feb. 15, 2018

(30) Foreign Application Priority Data
Mar. 11, 2015 (JP) ................................. 2015-048760

(51) Int. Cl.
| | |
|---|---|
| *G03F 7/09* | (2006.01) |
| *G03F 7/004* | (2006.01) |
| *C07C 67/347* | (2006.01) |
| *C07C 69/753* | (2006.01) |
| *C08F 20/36* | (2006.01) |
| *C09D 133/14* | (2006.01) |
| *G03F 7/075* | (2006.01) |
| *G03F 7/16* | (2006.01) |
| *H01L 21/308* | (2006.01) |

(52) U.S. Cl.
CPC .......... *G03F 7/0046* (2013.01); *C07C 67/347* (2013.01); *C07C 69/753* (2013.01); *C08F 20/36* (2013.01); *C09D 133/14* (2013.01); *G03F 7/0752* (2013.01); *G03F 7/0757* (2013.01); *G03F 7/094* (2013.01); *G03F 7/168* (2013.01); *H01L 21/3086* (2013.01); *C07C 2601/02* (2017.05); *C07C 2604/00* (2017.05)

(58) Field of Classification Search
CPC ....... C07C 69/38; C07C 69/74; C07C 69/753; C07C 2604/00; G03F 7/0752; G03F 7/094; H01L 21/3086
USPC ...................................................... 430/271.1
See application file for complete search history.

(56) References Cited

U.S. PATENT DOCUMENTS

| | | | | |
|---|---|---|---|---|
| 5,759,666 A | * | 6/1998 | Carlson | .............. C08G 18/0814 428/123 |
| 2005/0215713 A1 | * | 9/2005 | Hessell | .................. C08G 59/24 525/162 |

FOREIGN PATENT DOCUMENTS

| | | |
|---|---|---|
| JP | 2008-164806 A | 7/2008 |
| WO | 2008/062888 A1 | 5/2008 |
| WO | 2008/126804 A1 | 10/2008 |
| WO | 2011/108365 A1 | 9/2011 |

OTHER PUBLICATIONS

Apr. 5, 2016 International Search Report issued in International Patent Application No. PCT/JP2016/053534.
Apr. 5, 2016 Written Opinion of the International Searching Authority issued in International Patent Application No. PCT/JP2016/053534.

* cited by examiner

*Primary Examiner* — Daborah Chacko-Davis
(74) *Attorney, Agent, or Firm* — Oliff PLC

(57) ABSTRACT

A method forms a resist underlayer film that has high resistance to dry etching using a gas containing a fluorocarbon. A method for forming a resist underlayer film includes the steps of: applying to a substrate a resist underlayer film-forming composition containing a fullerene derivative in which one to six molecules of malonic acid diester of the following Formula (1):

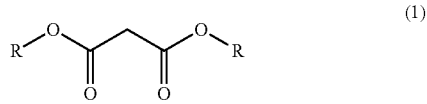

(1)

wherein two Rs are each independently a $C_{1-10}$ alkyl group, are added to one molecule of fullerene, a compound having at least two epoxy groups, and a solvent; and baking the substrate applied with the resist underlayer film-forming composition at least one time at a temperature of 240° C. or higher under an atmosphere of nitrogen, argon, or a mixture thereof.

3 Claims, No Drawings

METHOD FOR FORMING RESIST UNDERLAYER FILM

TECHNICAL FIELD

The present invention relates to a method for forming a resist underlayer film used in a lithography process that is a film obtained from a composition containing a fullerene derivative as a solid content.

BACKGROUND ART

In a lithography process for production of a semiconductor device, a technology of forming a resist pattern in a desired shape by providing a resist underlayer film before formation of a photoresist film has been known. The following Patent Documents 1 and 2 describe a resist underlayer film-forming composition prepared using a fullerene derivative. In the fullerene derivative used in the invention described in Patent Document 2, it is known that an adduct (modified group) is decomposed by heating to produce a carboxyl group. Specifically, when a solution containing a fullerene derivative having the adduct (modified group) is applied and baked at a temperature at which the adduct (modified group) is decomposed, the carbon content ratio of a film to be formed can be increased as compared with that before decomposition.

In conventional formation of a resist underlayer film from a resist underlayer film-forming composition containing a fullerene derivative, the resist underlayer film-forming composition is applied to a substrate, and the substrate is baked on a hot plate at a temperature of 180° C. to 400° C. for a predetermined time, to form the resist underlayer film. The baking is carried out in the air.

PRIOR ART DOCUMENTS

Patent Documents

Patent Document 1: International Publication No. WO2008/126804
Patent Document 2: International Publication No. WO2011/108365

SUMMARY OF THE INVENTION

Problem to be Solved by the Invention

In formation of the resist underlayer film from the resist underlayer film-forming composition containing a fullerene derivative, improved resistance to dry etching using a gas containing a fluorocarbon is desired. It is considered that during baking in the formation of the resist underlayer film, decomposition of not only an adduct (modified group) of the fullerene derivative but also a fullerene skeleton makes it difficult to improve the dry etching resistance of the resist underlayer film to be obtained.

An object of the present invention is to provide a method for forming, from a resist underlayer film-forming composition containing a fullerene derivative, a resist underlayer film that has high resistance to dry etching using a gas containing a fluorocarbon, that is, a resist underlayer film that has low dry etching rate.

Means for Solving the Problems

The inventors of the present invention have investigated the problems, and as a result, found that about 20% by volume of oxygen contained in the air during baking affects dry etching resistance of a resist underlayer film to be formed. When baking is carried out under an atmosphere of nitrogen, argon, or a mixture thereof, the problems can be solved.

As a first aspect, the present invention is a method for forming a resist underlayer film comprising the steps of: applying to a substrate a resist underlayer film-forming composition containing a fullerene derivative in which one to six molecules of malonic acid diester of the following Formula (1):

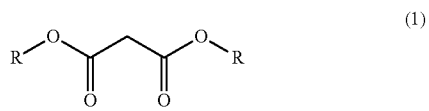

(wherein two Rs are each independently a $C_{1-10}$ alkyl group) are added to one molecule of fullerene, a compound having at least two epoxy groups, and a solvent; and baking the substrate applied with the resist underlayer film-forming composition at least one time at a temperature of 240° C. or higher under an atmosphere of nitrogen, argon, or a mixture thereof.

For example, a baking temperature under the atmosphere is 750° C. or lower.

It is preferable that an oxygen concentration of the atmosphere be 0.01 ppm to 100 ppm from the viewpoint of suppressing oxidation of the resist underlayer film to be formed. The oxygen concentration can be measured by a commercially available oxygen concentration meter.

As a second aspect, the present invention is a method for forming a pattern comprising the steps of: applying an intermediate layer-forming composition to the resist underlayer film, followed by baking, to form a silicon-containing intermediate layer; forming a resist film on the silicon-containing intermediate layer; carrying out at least exposure and development for the resist film to form a resist pattern; and dry etching the silicon-containing intermediate layer using a gas containing a fluorocarbon through the resist pattern serving as a mask.

Effects of the Invention

In the resist underlayer film formed by the present invention, oxidation is suppressed as compared with a resist underlayer film formed through baking in the air, and the resistance to dry etching using a gas containing a fluorocarbon can be improved.

MODES FOR CARRYING OUT THE INVENTION

A fullerene derivative contained in the resist underlayer film-forming composition used in the present invention is, for example, a compound of the following Formula (2):

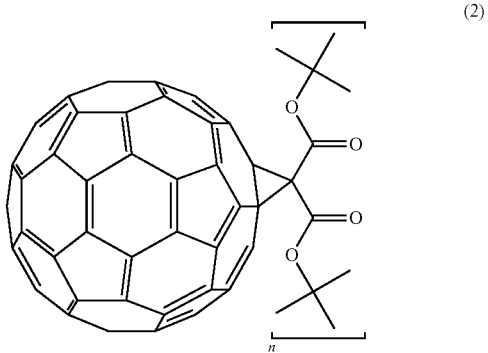

(2)

(wherein n is an integer of 1 to 6) in which both two Rs in the aforementioned Formula (I) are a tert-butyl group. However, the fullerene derivative is not specified to the fullerene derivative of Formula (2).

The fullerene derivative contained in the resist underlayer film-forming composition used in the present invention can contain as a main component a tetra-adduct in which four molecules of malonic acid diester of Formula (1) are added to one molecule of fullerene.

The fullerene to which the malonic acid diester is added is not limited to $C_{60}$, and $C_{70}$, or a mixture of $C_{60}$ and $C_{70}$ can be used. In addition to $C_{60}$ and $C_{70}$, a mixture containing a high-order fullerene can be also used. The specification defines that the high-order fullerene collectively refers to fullerenes having more than 70 carbon atoms (e.g., $C_{76}$, $C_{82}$, $C_{84}$, $C_{90}$, and $C_{96}$). The use of the mixture can reduce the cost as compared with use of $C_{60}$ or $C_{70}$.

It is preferable that an epoxy compound contained in the resist underlayer film-forming composition used in the present invention be a compound having at least two epoxy groups. Examples of such an epoxy compound include YH434L (manufactured by NSCC Epoxy Manufacturing Co., Ltd.), GT401 (manufactured by Daicel Corporation), TETRAD-C (manufactured by MITSUBISHI GAS CHEMICAL COMPANY, INC.), and HP-4700 (manufactured by DIC Corporation). For example, the epoxy compound is contained in an amount of 0.1% by mass to 500% by mass, and preferably 1% by mass to 100% by mass relative to the fullerene derivative.

The resist underlayer film-forming composition used in the present invention can further contain a surfactant. Examples of the surfactant include fluorosurfactants including Eftop (registered trademark) EF301, EF303, and EF352 (manufactured by Mitsubishi Materials Electronic Chemicals Co., Ltd.), MEGAFACE (registered trademark) F171, F173, R-30, R-40, and R-40LM (manufactured by DIC Corporation), Fluorad FC430 and FC431 (manufactured by Sumitomo 3M, Ltd.), and Asahi Guard (registered trademark) AG710, and Surfion (registered trademark) S-382, SC101, SC102, SC103, SC104, SC105, and SC106 (manufactured by Asahi Glass Co., Ltd.), and organosiloxane polymer KP341 (manufactured by Shin-Etsu Chemical Co., Ltd.). One selected from the surfactants may be added, or two or more thereof may be added in combination. For example, the surfactant is contained in an amount of 0.01% by mass to 10% by mass, and preferably 0.1% by mass to 5% by mass relative to the fullerene derivative.

The resist underlayer film-forming composition used in the present invention can further contain an acid catalyst or a base catalyst. Examples of the acid catalyst include an onium salt, a diazomethane derivative, a glyoxime derivative, a bissulfone derivative, a β-ketosulfone derivative, a disulfone derivative, a nitrobenzyl sulfonate derivative, a sulfonic acid ester derivative, and a sulfonic acid ester derivative of N-hydroxyimide compound. Examples of the base catalyst include an imidazole compound, a quaternary ammonium salt, a phosphonium salt, an amine compound, an aluminum chelate compound, and an organic phosphine compound. Specific examples thereof include 2-methylimidazole, 2-ethyl-4-methylimidazole, 1,8-diaza-bicyclo(5,4,0)undecene-7, an amine compound such as trimethylamine, benzyldimethylamine, triethylamine, dimethylbenzylamine and 2,4,6-trisdimethylaminomethylphenol, and a salt thereof, a quaternary ammonium salt such as tetramethylammonium chloride, benzyltrimethylammonium bromide, benzyltriethylammonium chloride, and tetrabutylammonium bromide, aluminum chelate, and an organic phosphine compound such as tetra-n-butylphosphonium benzotriazolate, and tetra-n-butylphosphonium-o,o-diethyl phosphorodithioate. One selected from the acid catalysts or base catalysts may be added, or two or more thereof may be added in combination. For example, the acid catalyst or base catalyst is contained in an amount of OA % by mass to 50% by mass, and preferably 0.5% by mass to 40% by mass relative to the fullerene derivative. The acid catalyst and base catalyst promote a decomposition reaction of adduct (modified group) of the fullerene derivative and a crosslinking reaction.

The resist underlayer film-forming composition used in the present invention is used in a uniform solution state in which the components described above are dissolved in a solvent. Examples of the solvent include propylene glycol monomethyl ether acetate, cyclohexanone, 2-heptanone, ethyl lactate, o-xylene, toluene, o-dichlorobenzene, propylene glycol monomethyl ether, propylene glycol monopropyl ether, 1-methyl-2-pyrrolidone, and a γ-butyrolactone. One selected from the solvents may be used, or two or more thereof may be used in combination.

It is preferable that the prepared resist underlayer film-forming composition be used, for example, after filtration through a filter having a pore diameter of 0.1 μm or smaller. The resist underlayer film-forming composition after the filtration has excellent shelf stability at room temperature for an extended period.

Hereinafter, the method for forming a resist underlayer film and the method for forming a pattern of the present invention will be further specifically described. The resist underlayer film-forming composition is applied to a substrate (e.g., a semiconductor substrate of silicon in which a silicon oxide film, a silicon nitride film, or a silicon oxide nitride film is formed, a silicon nitride substrate, a quartz substrate, a glass substrate (including alkali-free glass, low alkaline glass, and a crystalline glass), and a glass substrate having an ITO film) by an appropriate coating method such as a spinner and a coater. Subsequently, the substrate coated with the resist underlayer film-forming composition is baked using heating means such as a hot plate under an atmosphere of nitrogen, argon, or a mixture thereof, to form a resist underlayer film. As a baking condition, an appropriate value is selected from a temperature of 240° C. or higher and a time of 0.3 minutes to 10 minutes. In the present invention, it is preferable that the baking temperature be a temperature at which a fullerene skeleton is not thermally decomposed. In the present invention, the upper limit of baking temperature can be set to a temperature higher than that in the case of baking in the air. The upper limit of baking temperature may be set to 500° C. or higher, and for example, 750° C. Within a temperature range in which the fullerene skeleton is not thermally decomposed, the higher the baking temperature is, the higher the density of the film to be formed can be made. Therefore, the lower limit thereof can be set to 350° C. The baking condition may be changed, and the baking may be carried out in two or more steps to form the resist underlayer film. When the baking is carried out in two steps to form the resist underlayer film, it is preferable that the second baking temperature be set to a temperature higher than the first baking temperature from the viewpoint of forming a compact film. For example, the first baking temperature may be set to an appropriate temperature within a range of 240° C. to 600° C., and the second baking temperature may be set to a temperature that is higher than the first baking temperature and within a range of 500° C. to 750° C.

The thickness of the formed resist underlayer film is 0.01 µm to 3.0 µm, and for example, 0.05 µm to 1.0 µm.

To the resist underlayer film, an intermediate layer-forming composition is applied by an appropriate coating method such as a spinner and a coater. Examples of the intermediate layer-forming composition include a solution containing one or two or more of hydrolysate and/or hydrolysis-condensation product of alkoxysilane and a necessary additive, and a solution containing a commercially available polysilane and a necessary additive. Subsequently, the substrate is baked using heating means such as a hot plate to form a silicon-containing intermediate layer. As a baking condition, an appropriate value is selected from a temperature of 180° C. to 300° C. and a time of 0.3 minutes to 10 minutes.

On the silicon-containing intermediate layer, a resist film is formed. The resist film can be formed by a general method, that is, applying a resist solution to the intermediate layer, followed by baking. The used resist solution is not particularly limited, and examples thereof include APEX-E (trade name) manufactured by Rohm and Haas Electronic Materials LLC, PAR710 (trade name) manufactured by Sumitomo Chemical Co., Ltd., and SEPR430 (trade name) manufactured by Shin-Etsu Chemical Co., Ltd.

Further, exposure is carried out through a photomask (reticle) to form a resist pattern from the resist film. In the exposure, for example, a KrF excimer laser, an ArF excimer laser, or extreme ultraviolet light (EUV) can be used. After the exposure, post exposure bake (PEB) is carried out, if necessary. Subsequently, development is carried out.

When a positive type resist solution is used, an alkaline developer is used in development. Examples of the alkaline developer include an aqueous solution of alkali metal hydroxide such as potassium hydroxide and sodium hydroxide, an aqueous solution of quaternary ammonium hydroxide such as tetramethylammonium hydroxide, tetraethylammonium hydroxide, and choline, and an aqueous solution of amine such as ethanolamine, propylamine, and ethylenediamine. To the developer, a surfactant can be further added.

A development condition is appropriately selected from a development temperature of 5° C. to 50° C. and a development time of 10 seconds to 300 seconds. In the present invention, development can be easily carried out at room temperature using a 2.38% by mass tetramethylammonium hydroxide aqueous solution, which is generally used in development of photoresist.

The silicon-containing intermediate layer is dry etched through the formed resist pattern serving as a mask using a gas containing a fluorocarbon. Examples of the fluorocarbon used herein include $CF_4$, $CHF_3$, $CH_2F_2$, and $C_4F_8$. As the gas containing a fluorocarbon, a mixed gas of the fluorocarbon and an inert gas such as argon can be used.

Hereinafter, the present invention will be specifically described by the following Synthesis Examples and Examples. However, the present invention is not limited to the Examples.

EXAMPLES

Synthesis Example 1

In a reactor, 9.80 g of di-tert-butyl malonate (manufactured by Aldrich) was placed under nitrogen flow, and 150 cm$^3$ of 1,2,4-trimethylbenzene and 6.50 g of diazabicyclo [5.4.0]-7-undecene (1,8-diazabicyclo[5.4.0]undec-7-ene, manufactured by Tokyo Chemical Industry Co., Ltd.) were further added. The temperature of the mixture was adjusted to 4° C. with stirring.

To the reaction liquid obtained after temperature adjustment, a dark purple solution obtained by dissolving 10.9 g of iodine (manufactured by Wako Pure Chemical Industries, Ltd.) in 130 cm$^3$ of 1,2,4-trimethylbenzene was gradually added dropwise. During dropwise addition, the temperature inside a flask was controlled to be 11° C. using an ice bath. After completion of dropwise addition, the temperature of the reaction liquid was returned to room temperature. The reaction liquid in the flask was in a state of brown suspension.

Subsequently, a solution obtained by dissolving 5.00 g of fullerene mixture (containing $C_{60}$, $C_{70}$, and high-order fullerenes other than $C_{60}$ and $C_{70}$, manufactured by Frontier Carbon Corporation) in 350 cm$^3$ of 1,2,4-trimethylbenzene was added to the reaction liquid in the reactor with stirring. The high-order fullerene herein is defined in the specification as a generic term for fullerenes having more than 70 carbon atoms. To the reaction liquid in the flask, a solution obtained by diluting 6.90 g of diazabicyclo[5.4.0]-7-undecene (1,8-diazabicyclo[5.4.0]undec-7-ene, manufactured by Tokyo Chemical Industry Co., Ltd.) with 5 cm$^3$ of 1,2,4-trimethylbenzene was then gradually added dropwise with stirring. The mixture was stirred at room temperature for 6.5 hours, resulting in a reaction.

For the obtained reaction liquid, a reaction layer (organic phase) was washed with a saturated sodium sulfite aqueous solution four times. The resulting organic phase was washed with 100 cm$^3$ of 1 N sulfuric acid aqueous solution twice, and washed with 200 cm$^3$ of pure water three times. The solvent (1,2,4-trimethylbenzene) was removed under reduced pressure, to obtain 9.50 g of red brown solid.

The obtained solid was separated by silica gel chromatography using a mixed solvent of n-hexane and ethyl acetate, to obtain a fullerene derivative (malonic acid di-tert-butyl ester adduct).

Preparation Example 1

In 1.0 g of the fullerene derivative obtained in Synthesis Example 1, 0.15 g of epoxy compound of the following Formula (3) (trade name: YH434L manufactured by NSCC Epoxy Manufacturing Co., Ltd.) and 0.001 g of MEGA-FACE (registered trademark) R-40 (manufactured by DIC Corporation) as a surfactant were mixed, and the mixture was dissolved in 7.0 g of propylene glycol monomethyl ether acetate to obtain a solution. Subsequently, the solution was filtered through a microfilter made of polyethylene with a pore diameter of 0.10 μm, and then through a microfilter made of polyethylene with a pore diameter of 0.05 μm to prepare a resist underlayer film-forming composition (solution).

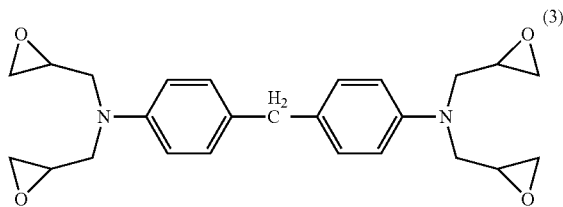 [SMILES: c1cc(N(CC2CO2)CC2CO2)ccc1Cc1ccc(N(CC2CO2)CC2CO2)cc1]

(3)

Comparative Preparation Example 1

In 1 g of cresol novolak resin (commercially available product, weight average molecular weight: 4,000), 10.34 g of propylene glycol monomethyl ether and 2.59 g of cyclohexanone were dissolved to prepare a resist underlayer film-forming composition (solution) to be used in a lithography process for a multilayer film.

The resist underlayer film-forming composition obtained in Preparation Example 1 was applied to silicon wafers in "CLEAN TRACK ACT-S" manufactured by Tokyo Electron Limited. Each silicon wafer was then baked independently at a temperature of 240° C., 300° C., 350° C., or 400° C. for 2 minutes on a hot plate under a nitrogen atmosphere, in which nitrogen gas had been introduced for 10 or more hours, to form a resist underlayer film (thickness: 0.05 μm).

[Measurement of Optical Parameter]

The refractive indexes (n value) of the formed resist underlayer films were measured at a wavelength of 633 nm using a spectroscopic ellipsometer (VUV-VASE VU-302, manufactured by J. A. Woollam Co.). The results are shown in Table 1. This suggests that as the baking temperature is increased, the n value increases and the film density increases.

TABLE 1

| Baking temperature | Refractive index (n value) |
|---|---|
| 240° C. | 1.82 |
| 300° C. | 1.86 |
| 350° C. | 1.93 |
| 400° C. | 1.97 |

The resist underlayer film-forming composition obtained in Preparation Example 1 was applied to silicon wafers using a spin coater. Subsequently, each silicon wafer was baked independently at a temperature of 240° C. or 350° C. for 1 minute on a hot plate under a nitrogen atmosphere, in which nitrogen gas had been introduced for 10 or more hours or on a hot plate in the air, to form a resist underlayer film (thickness: 0.20 μm). The resist underlayer film formed by baking at 240° C. under a nitrogen atmosphere was designated as Example 1. The resist underlayer film formed by baking at 350° C. under a nitrogen atmosphere was designated as Example 2. The resist underlayer film formed by baking at 240° C. in the air was designated as Comparative Example 1. The resist underlayer film formed by baking at 350° C. in the air was designated as Comparative Example 2. The resist underlayer film-forming composition obtained in Comparative Preparation Example 1 was applied to a silicon wafer using a spin coater. The silicon wafer was then baked at 205° C. for 1 minute on a hot plate in the air to form a resist underlayer film (thickness: 0.20 μm).

[Measurement of Dry Etching Rate]

In measurement of dry etching rate, the following etching device and etching gas were used.

Etching device: RIE-10NR (manufactured by SAMCO INC.)

Etching gas: $CF_4$

The dry etching rates of the resist underlayer films of Examples 1 and 2 and Comparative Examples 1 and 2 were measured. Further, the dry etching rate of the resist underlayer film formed from the resist underlayer film-forming composition obtained in Comparative Preparation Example 1 was measured. Values of the former dry etching rates when the latter dry etching rate was 1 were calculated. The values are referred to as dry etching rate ratio. The results are shown in Table 2 below.

TABLE 2

| Resist underlayer film | Baking environment | Baking temperature | Dry etching rate ratio |
|---|---|---|---|
| Comparative Example 1 | Air | 240° C. | 1.01 |
| Example 1 | Nitrogen | 240° C. | 0.94 |
| Comparative Example 2 | Air | 350° C. | 0.93 |
| Example 2 | Nitrogen | 350° C. | 0.75 |

In the resist underlayer films formed by baking under a nitrogen atmosphere, the dry etching rate ratios are smaller than those of the resist underlayer films formed by baking in the air. Specifically, the results show that the resistance to dry etching using $CF_4$ of the resist underlayer film obtained by baking under a nitrogen atmosphere is improved.

[Elemental Analysis]

The resist underlayer films in Comparative Example 1 and Example 2 were subjected to elemental analysis. The results of the elemental analysis are as shown in Table 3 below. In the elemental analysis, the following Rutherford backscattering spectrometry (RBS) device was used.

Analyzer: High-resolution RBS system HRBS500 (manufactured by Kobe Steel, Ltd.)

TABLE 3

| | % by mass | | |
|---|---|---|---|
| | C | H | O |
| Comparative Example 1 | 72.0 | 22.1 | 5.9 |
| Example 2 | 75.5 | 20.8 | 3.7 |

As seen from the results of Table 3, in the resist underlayer film formed by baking at 350° C. under a nitrogen atmosphere, the carbon concentration is increased, and the hydrogen concentration and the oxygen concentration are decreased as compared with the resist underlayer film formed by baking at 240° C. in the air.

The invention claimed is:

1. A method for forming a resist underlayer film comprising:

applying to a substrate a resist underlayer film-forming composition containing:
  a compound having at least two epoxy groups,
  a solvent, and
  a fullerene derivative, in which one to six molecules of malonic acid diester of the following Formula (1) are added to one molecule of fullerene,

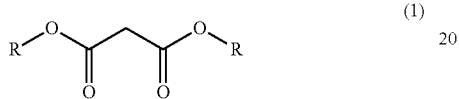

(1)

where two Rs are each independently a $C_{1-10}$ alkyl group; and baking the substrate applied with the resist underlayer film-forming composition under an atmosphere of nitrogen, argon, or a mixture thereof to form the resist underlayer film, the baking comprising:
  a first baking step performed at a first baking temperature of 240° C. or higher and 600° C. or lower under the atmosphere, and
  a second baking step performed at a second baking temperature in a range of from 500° C. to 750° C. under the atmosphere, the second baking temperature being higher than the first baking temperature,
wherein an oxygen concentration under the atmosphere is in a range of from 0.01 ppm to 100 ppm.

2. The method for forming a resist underlayer film according to claim 1, wherein the resist underlayer film-forming composition further contains a surfactant.

3. A method for forming a pattern comprising:
applying a silicon-containing intermediate layer-forming composition to the resist underlayer film formed by the method according to claim 1, followed by baking, to form a silicon-containing intermediate layer;
forming a resist film on the silicon-containing intermediate layer;
carrying out at least exposure and development for the resist film to form a resist pattern; and
dry etching the silicon-containing intermediate layer using a gas containing a fluorocarbon through the resist pattern serving as a mask.

* * * * *